(12) United States Patent
Kamada et al.

(10) Patent No.: US 9,918,975 B2
(45) Date of Patent: Mar. 20, 2018

(54) METHOD FOR IMPROVING DISSOLUTION OF ANTICOAGULANT AGENT

(71) Applicant: Daiichi Sankyo Company, Limited, Tokyo (JP)

(72) Inventors: Makoto Kamada, Kanagawa (JP); Gaku Sekiguchi, Kanagawa (JP); Motonori Kidokoro, Kanagawa (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 87 days.

(21) Appl. No.: 13/622,693

(22) Filed: Sep. 19, 2012

(65) Prior Publication Data

US 2013/0022683 A1    Jan. 24, 2013

Related U.S. Application Data

(63) Continuation of application No. PCT/JP2011/055956, filed on Mar. 14, 2011.

(30) Foreign Application Priority Data

Mar. 19, 2010  (JP) .................................. 2010-063694

(51) Int. Cl.
  *A61K 31/444* (2006.01)
  *A61K 9/16* (2006.01)
  *A61K 9/20* (2006.01)

(52) U.S. Cl.
  CPC .......... *A61K 31/444* (2013.01); *A61K 9/1623* (2013.01); *A61K 9/1635* (2013.01);
  (Continued)

(58) Field of Classification Search
  None
  See application file for complete search history.

(56) References Cited

U.S. PATENT DOCUMENTS 4,361,545 A   11/1982  Powell et al.
4,582,570 A    4/1986  Mix
(Continued)

FOREIGN PATENT DOCUMENTS

CA        2434976      8/2002
CN      101652139      2/2010
(Continued)

OTHER PUBLICATIONS

Shawn et al. ("Shawn", Int. J. Pharm, 2003, 250(1), pp. 3-11).*
(Continued)

*Primary Examiner* — Jianfeng Song
(74) *Attorney, Agent, or Firm* — Locke Lord LLP

(57) ABSTRACT

It is desired to provide a pharmaceutical composition containing a compound represented by formula (I) or a pharmaceutically acceptable salt thereof, or a solvate thereof, which exhibits an inhibitory effect on activated blood coagulation factor X, and is useful as an agent for preventing and/or treating thrombosis, wherein the pharmaceutical composition exhibits favorable dissolution properties. The present invention provides a method for producing a pharmaceutical composition containing a compound represented by formula (I), comprising the step of mixing a compound represented by formula (I) or a pharmaceutically acceptable salt thereof, or a solvate thereof, one or more excipients selected from the group consisting of a sugar alcohol and a water-swelling additive, a disintegrant, and a binder under conditions for keeping the maximum water content of the granules during granulation at 10% or less.

14 Claims, 3 Drawing Sheets

(52) U.S. Cl.
CPC .......... *A61K 9/1652* (2013.01); *A61K 9/1694* (2013.01); *A61K 9/2077* (2013.01)

(56) References Cited

U.S. PATENT DOCUMENTS

| | | |
|---|---|---|
| 5,055,600 A | 10/1991 | Wagner |
| 5,091,191 A | 2/1992 | Oda et al. |
| 5,202,129 A | 4/1993 | Samejima et al. |
| 5,677,469 A | 10/1997 | Van Eikeren et al. |
| 5,958,453 A | 9/1999 | Ohno et al. |
| 7,081,256 B2 | 7/2006 | Kubota et al. |
| 7,192,968 B2 | 3/2007 | Yoshino et al. |
| 7,342,014 B2 | 3/2008 | Ohta et al. |
| 7,365,205 B2 | 4/2008 | Ohta et al. |
| 7,547,786 B2 | 6/2009 | Nagasawa et al. |
| 7,576,135 B2 | 8/2009 | Ohta et al. |
| 7,605,180 B2 | 10/2009 | Ninomiya et al. |
| 7,674,904 B2 | 3/2010 | Doshan et al. |
| 2002/0044968 A1 | 4/2002 | van Lengerich |
| 2002/0160048 A1 | 10/2002 | Bechtold-Peters et al. |
| 2003/0017198 A1* | 1/2003 | Yeh ..................... A61K 9/1694 424/465 |
| 2003/0086972 A1 | 5/2003 | Appel et al. |
| 2004/0052845 A1 | 3/2004 | Appel et al. |
| 2005/0020645 A1 | 1/2005 | Ohta et al. |
| 2005/0119486 A1 | 6/2005 | Ohta et al. |
| 2005/0245565 A1 | 11/2005 | Ohta et al. |
| 2006/0252837 A1 | 11/2006 | Ohta et al. |
| 2006/0275357 A1 | 12/2006 | Oomura et al. |
| 2007/0135476 A1 | 6/2007 | Nagasawa et al. |
| 2008/0015215 A1 | 1/2008 | Ohta et al. |
| 2009/0105491 A1 | 4/2009 | Sato et al. |
| 2009/0192313 A1 | 7/2009 | Nagasawa et al. |
| 2009/0270446 A1 | 10/2009 | Ohta et al. |
| 2009/0281074 A1 | 11/2009 | Ohta et al. |
| 2010/0081685 A1 | 4/2010 | Kojima |
| 2011/0045028 A1 | 2/2011 | Iinuma et al. |
| 2011/0229567 A1 | 9/2011 | Hirata et al. |
| 2012/0114711 A1 | 5/2012 | Kamada |
| 2013/0004550 A1 | 1/2013 | Kanamaru et al. |
| 2013/0005763 A1 | 1/2013 | Kanamaru et al. |
| 2013/0012535 A1 | 1/2013 | Kanamaru et al. |
| 2013/0022683 A1 | 1/2013 | Kamada et al. |
| 2013/0337064 A1 | 12/2013 | Kojima |
| 2014/0171464 A1 | 6/2014 | Ishidoh |

FOREIGN PATENT DOCUMENTS

| | | |
|---|---|---|
| CN | 102058889 | 5/2011 |
| EP | 1103253 | 5/2001 |
| EP | 1 270 006 | 1/2003 |
| EP | 2140867 | 1/2010 |
| JP | H02-704 | 1/1990 |
| JP | H08-73345 | 3/1996 |
| JP | 09-165346 A | 6/1997 |
| JP | H09-309829 | 12/1997 |
| JP | 2001-151672 | 6/2001 |
| JP | 2003-73274 | 3/2003 |
| JP | 2004-505907 | 2/2004 |
| JP | 2004-518710 | 6/2004 |
| JP | 2005-263816 | 9/2005 |
| RU | 2 271 805 | 8/2004 |
| WO | 02/064124 | 8/2002 |
| WO | 03/000657 | 1/2003 |
| WO | 03/000680 | 1/2003 |
| WO | 03/016302 | 2/2003 |
| WO | 03/070279 | 8/2003 |
| WO | 03/097102 | 11/2003 |
| WO | 2004/058715 | 7/2004 |
| WO | 2004/110448 | 12/2004 |
| WO | 2005/047296 | 5/2005 |
| WO | 2007/032498 | 3/2007 |
| WO | 2008/066102 | 6/2008 |
| WO | 2008/129846 | 10/2008 |
| WO | 2008/156159 | 12/2008 |
| WO | 2010/147169 | 12/2010 |
| WO | 2011/102504 | 8/2011 |
| WO | 2011/102505 | 8/2011 |
| WO | 2011/102506 | 8/2011 |
| WO | 2011/115067 | 9/2011 |

OTHER PUBLICATIONS

Vippangupta, 2001, Advanced Drug Delivery Reviews, 48, 3-26.*
Braga et al, 2009, Struct. Bond, 132, 25-50.*
Ulrich Mueller, Inorganic Structural Chemistry 1993, 14-15.*
Armin H. Gerhardt ("Gerhardt", J. of GXP Compliance, 2009, 13(1), pp. 58-66).*
Vippagunta et al. "Crystalline Solids," Advanced Drug Delivery Reviews, 2001, 48, pp. 18.*
Müller, Inorganic Chemistry, p. 14-15, 1993.*
International Search Report, issued in PCT/JP2010/060261, mailed Sep. 21, 2010 (PCT/JP2010/060261 is an international application corresponding to related U.S. Appl. No. 13/328,847).
Written Opinion of the International Searching Authority, issued in PCT/JP2010/060261, mailed Sep. 21, 2010 (PCT/JP2010/060261 is an international application corresponding to related U.S. Appl. No. 13/328,847).
International Preliminary Report on Patentability, issued in PCT/JP2010/060261, mailed Dec. 20, 2011 (PCT/JP2010/060261 is an international application corresponding to related U.S. Appl. No. 13/328,847).
International Search Report, issued in PCT/JP2011/055956, mailed Apr. 26, 2011 (PCT/JP2011/055956 is an international application corresponding to the present U.S. Appl. No. 13/622,693).
Written Opinion of the International Searching Authority, issued in PCT/JP2011/055956, mailed Apr. 26, 2011 (PCT/JP2011/055956 is an international application corresponding to the present U.S. Appl. No. 13/622,693).
International Preliminary Report on Patentability, issued in PCT/JP2011/055956, mailed Oct. 23, 2012 (PCT/JP2011/055956 is an international application corresponding to the present U.S. Appl. No. 13/622,693).
International Search Report, issued in PCT/JP2012/070314, mailed Oct. 23, 2012 (PCT/JP2012/070314 is an international application corresponding to related U.S. Appl. No. 14/237,884).
Written Opinion of the International Searching Authority, issued in PCT/JP2012/070314, mailed Oct. 23, 2012 (PCT/JP2012/070314 is an international application corresponding to related U.S. Appl. No. 14/237,884).
International Preliminary Report on Patentability, issued in PCT/JP2012/070314, mailed Feb. 11, 2014 (PCT/JP2012/070314 is an international application corresponding to related U.S. Appl. No. 14/237,884).
International Search Report, issued in PCT/JP2008/000791, mailed Jun. 24, 2008 (PCT/JP2008/000791 is an international application corresponding to related U.S. Appl. Nos. 12/569,057 & 13/968,776).
Written Opinion of the International Searching Authority, issued in PCT/JP2008/000791, mailed Jun. 24, 2008 (PCT/JP2008/000791 is an international application corresponding to related U.S. Appl. Nos. 12/569,057 & 13/968,776).
International Preliminary Report on Patentability, issued in PCT/JP2008/000791, mailed Oct. 20, 2009 (PCT/JP2008/000791 is an international application corresponding to related U.S. Appl. Nos. 12/569,057 & 13/968,776).
Extended Search Report, issued in European Patent Application No. 08720658.7, mailed Jun. 3, 2013 (EP 08720658.7 is the European corresponding to related U.S. Appl. Nos. 12/569,057 & 12/968,776).
Turpie, A. G.G. Turpie, "Oral, Direct Factor Xa Inhibitors in development for the prevention and Treatment of Thromboembolic Diseases," Arteriosclerosis, Thrombosis, and Vascular Biology, vol. 27, No. 6, pp. 1238-1247, XP002672841, Mar. 22, 2007.
Jacob, et al., "Novel Co-Processed Excipients of Mannitol and Microcrystalline Cellulose for Preparing Fast Dissolving Tablets of Glipizide," Indian Journal of Pharmaceutical Sciences, pp. 633-639, Sep. 1, 2007.

(56) References Cited

OTHER PUBLICATIONS

Shin-Etsu Chemical Co., Ltd., Pharmacoat, "Film Coating Material and Binder," pp. 1-12, Feb. 2005.

Serajuddin, A.T.M., "Salt formation to improve drug solubility" Advanced Drug Delivery Reviews, vol. 59, pp. 603-616, May 2007.

Nassab, et al., "Physicochemical characterization of meloxicam-mannitol binary system," Journal of Pharmaceutical and Biomedical Analysis 41:1191-1197, (2006).

Takeuchi, et al., "Tabletting of solid dispersion particles consisting of indomethacin and porous silica particles," Chem., Pharm., Bull., 53(5) 487-491 (2005).

Gombas, et al., "Study of Thermal Behaviour of Sugar Alcohols," Journal of Thermal Analysis and Calorimetry, vol. 73, pp. 615-621 (2003).

Jiho, Inc., "Handbook for new drug Approval Application 1993," pp. 128-133 (with partial English translation) (1993).

Chowdary, et al., "Effect of Selected Binders and Disintergrants on the Dissolution Rate Nimesulide from Tablets," Indian Journal of Pharmaceutical Sciences, vol. 62, Issue 3, pp. 224-228, Jun. 2000.

Chinese Search Report, issued in Chinese Application No. 2012800388139, dated Dec. 17, 2014 (CN2012800388139 is the Chinese application corresponding to related U.S. Appl. No. 14/237,884).

Hylek, E.M., "Drug evaluation: DU-176b, an oral, direct Factor Xa antagonist." Current Opinion in Investigational Drugs, 8, (9), 778-783 (2007).

Furugohri, T., et al., "DU-176b, A potent and orally active factor Xa inhibitor: In vitro and in vivo pharmacological profiles" Journal of Thrombosis and Haemostasis, 6(9), 1542-1549 (2008).

Supplementary European Search Report issued in European Application EP12822801, which corresponds to related U.S. Appl. No. 14/237,884, dated May 8, 2015.

Extended European Search Report dated June 18, 2014 corresponding to Application No. 11756252.0 (6 pages).

Notice of Opposition filed in the European Patent Office dated May 10, 2017 corresponding to European Patent No. 2,548,556 (Application No. 11756252.0) (8 pages).

L. Baert et al., "Influence of amount of granulation liquid on the drug release rate from pellets made by extrusion spheronisation," International Journal of Pharmaceutics, 95 (1993), pp. 135-141.

\* cited by examiner

METHOD FOR IMPROVING DISSOLUTION OF ANTICOAGULANT AGENT

This application is a continuation of International Application No. PCT/JP2011/055956, filed on Mar. 14, 2011, entitled "METHOD FOR IMPROVING DISSOLVABILITY OF ANTICOAGULANT", which claims the benefit of Japanese Patent Application Number JP 2010-063694, filed on Mar. 19, 2010, both of which are hereby incorporated by reference.

FIELD OF THE INVENTION

The present invention relates to a method for producing a pharmaceutical composition that exhibits favorable dissolution properties, containing a compound that exhibits an inhibitory effect on activated blood coagulation factor X (FXa), and that is useful as a preventative and/or therapeutic drug for thrombotic diseases.

BACKGROUND $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide represented by the following formula (I) (in the present specification, also referred to as compound I):

[Formula 1]

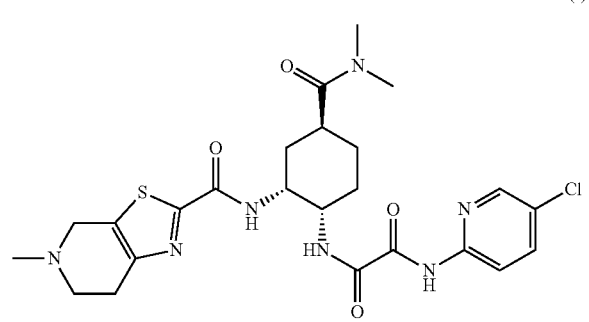

(I)

or a pharmaceutically acceptable salt thereof, or a solvate thereof (in the present specification, compound I, a pharmaceutically acceptable salt thereof, and solvates thereof are also collectively referred to as compound I, etc.) is known to exhibit a potent inhibitory effect on activated blood coagulation factor X and be useful as a pharmaceutical drug, particularly as an activated blood coagulation factor X inhibitor and/or an agent for preventing and/or treating thrombosis or embolism (Patent Documents 1 to 9).

Compound I is a basic compound that exhibits favorable solubility in strongly acidic aqueous solutions, but reduced solubility in neutral aqueous solutions (e.g., a neutral buffer). A pharmaceutical composition containing compound I, etc., wherein the pharmaceutical composition is coated with one or two or more coating agents selected from a cellulose derivative, a polyvinyl compound, an acrylic acid derivative, and a saccharide is known as a pharmaceutical composition having improved dissolution properties in the neutral region, containing compound I, etc. as an active ingredient (Patent Document 7). Moreover, Patent Document 9 discloses that the dissolution rate of compound I, etc. from a pharmaceutical composition containing compound I, etc. is improved by adjusting the proportion of compound I, etc. in the pharmaceutical composition.

CITATION LIST

Patent Documents

Patent Document 1: WO2003/000657
Patent Document 2: WO2003/000680
Patent Document 3: WO2003/016302
Patent Document 4: WO2004/058715
Patent Document 5: WO2005/047296
Patent Document 6: WO2007/032498
Patent Document 7: WO2008/129846
Patent Document 8: WO2008/156159
Patent Document 9: WO2010/147169

SUMMARY OF THE INVENTION

Technical Problem

An object of the present invention is to provide a method for producing a pharmaceutical composition containing compound I or a pharmaceutically acceptable salt thereof, or a solvate thereof as an active ingredient and having favorable dissolution properties in the neutral region, and a pharmaceutical composition obtained by the method.

Solution to Problem

As a result of conducting diligent studies, the present inventors have found that, surprisingly, a very simple method of keeping the maximum water content of granules during granulation at 10% or less in the production of granules containing compound I or a pharmaceutically acceptable salt thereof, or a solvate thereof can drastically improve the dissolution rate of compound I or a pharmaceutically acceptable salt thereof, or a solvate thereof from a pharmaceutical composition containing the granules and can also improve the variation in dissolution among tablets. Based on this finding, the present invention has been completed.

Specifically, the present invention relates to:
[1] a method for producing granules containing compound I or a pharmaceutically acceptable salt thereof, or a solvate thereof, the method comprising the step of granulating
(A) compound I or a pharmaceutically acceptable salt thereof, or a solvate thereof,
(B) one or more excipients selected from the group consisting of a sugar alcohol and a water-swelling additive,
(C) a disintegrant, and
(D) a binder
under conditions for keeping the maximum water content of the granules during granulation at 10% or less;
[2] the method according to [1], wherein the maximum water content of the granules during granulation is 8% or less;
[3] the method according to [1] or [2], wherein at least one or more sugar alcohols and at least one or more water-swelling additives are used as the excipients;
[4] the method according to any one of [1] to [3], wherein the sugar alcohol is mannitol, xylitol, or erythritol;
[5] the method according to any one of [1] to [4], wherein the sugar alcohol is mannitol;

[6] the method according to any one of [1] to [5], wherein the water-swelling additive is pregelatinized starch or crystalline cellulose;
[7] the method according to any one of [1] to [6], wherein the water-swelling additive is pregelatinized starch;
[8] the method according to [5] or [7], wherein the sugar alcohol is mannitol, and the water-swelling additive is pregelatinized starch;
[9] the method according to any one of [1] to [8], wherein the disintegrant is crospovidone or sodium carboxymethyl starch;
[10] the method according to any one of [1] to [9], wherein the disintegrant is crospovidone;
[11] the method according to any one of [1] to [10], wherein the binder is hydroxypropyl cellulose;
[12] the granulation according to any one of [1] to [11], wherein the granulation method is fluidized-bed granulation;
[13] the method according to any one of [1] to [12], wherein the component (A) is $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide p-toluenesulfonate monohydrate represented by the following formula (Ia) (in the present specification, also referred to as compound Ia):

[Formula 2]

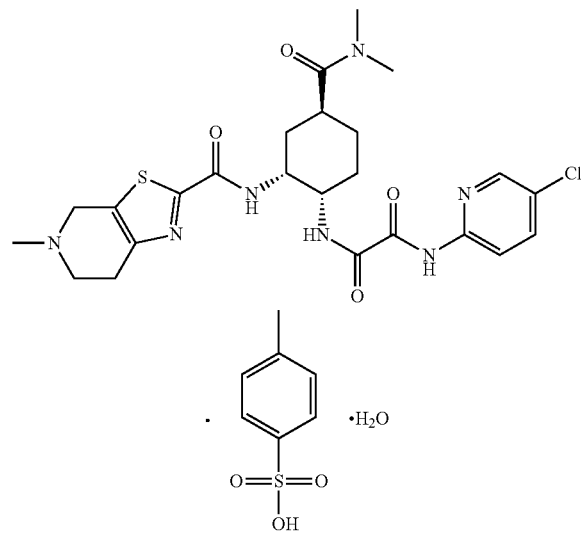

(Ia)

[14] granules obtained by a method according to any one of [1] to [13];
[15] a method for producing a pharmaceutical composition containing compound I or a pharmaceutically acceptable salt thereof, or a solvate thereof, the method comprising the step of granulating
(A) compound I or a pharmaceutically acceptable salt thereof, or a solvate thereof,
(B) one or more excipients selected from the group consisting of a sugar alcohol and a water-swelling additive,
(C) a disintegrant, and
(D) a binder
under conditions for keeping the maximum water content of the granules during granulation at 10% or less;
[16] the method according to [15], wherein the maximum water content of the granules during granulation is 8% or less;
[17] the method according to [15] or [16], wherein a sugar alcohol and a water-swelling additive are used as the excipients;
[18] the method according to any one of [15] to [17], wherein the sugar alcohol is mannitol, xylitol, or erythritol;
[19] the method according to any one of [15] to [18], wherein the sugar alcohol is mannitol;
[20] the method according to any one of [15] to [19], wherein the water-swelling additive is pregelatinized starch or crystalline cellulose;
[21] the method according to any one of [15] to [20], wherein the water-swelling additive is pregelatinized starch;
[22] the method according to [19] or [21], wherein the sugar alcohol is mannitol, and the water-swelling additive is pregelatinized starch;
[23] the method according to any one of [15] to [22], wherein the disintegrant is crospovidone or sodium carboxymethyl starch;
[24] the method according to any one of [15] to [23], wherein the disintegrant is crospovidone;
[25] the method according to any one of [15] to [24], wherein the binder is hydroxypropyl cellulose;
[26] the method according to any one of [15] to [25], wherein the granulation is fluidized-bed granulation;
[27] the method according to any one of [15] to [26], wherein the component (A) is compound Ia;
[28] the method according to any one of [15] to [27], further comprising the step of drying the obtained granules;
[29] the method according to any one of [15] to [28], further comprising the step of compressing the obtained granules;
[30] the method according to any one of [15] to [29], further comprising a coating step after the granulation step;
[31] the method according to [30], wherein the coating agent is one or more coating agents selected from the group consisting of a cellulose derivative and a polyvinyl compound;
[32] the method according to [30], wherein the coating agent is one or more coating agents selected from the group consisting of hypromellose, ethyl cellulose, and polyvinyl alcohol;
[33] a pharmaceutical composition obtained by a method according to any one of [15] to [32];
[34] the pharmaceutical composition according to [33], wherein when the composition is subjected to a dissolution test by the paddle method at a rotation speed of 50 rpm, the composition exhibits an mean dissolution rate of the compound represented by formula (I), in a dissolution medium having a pH of 6.8, of 60% or higher in 30 minutes after the start of the dissolution test and 70% or higher in 60 minutes after the start; and
[35] the pharmaceutical composition according to [33] or [34], wherein when the composition is subjected to a dissolution test by the paddle method at a rotation speed of 50 rpm, the composition exhibits an mean dissolution rate of the compound represented by formula (I), in a dissolution medium having a pH of 6.8, of 70% or higher in 30 minutes after the start of the dissolution test and 80% or higher in 60 minutes after the start.

Advantageous Effects of the Invention

The present invention provides a pharmaceutical composition containing compound I, etc. and having favorable dissolution properties in the neutral region.

BRIEF DESCRIPTION OF THE DRAWINGS

FIG. 1(a) is a graph showing the dissolution properties of compound I in a phosphate buffer of pH 6.8 for tablets (6 tablets per group) produced using granules granulated under granulation condition A and dried such that the water content of granules after drying was 4.0% or more (granulation condition A-1). The vertical axis shows dissolution rate (%), and the horizontal axis shows time (min).

Figure 1A:
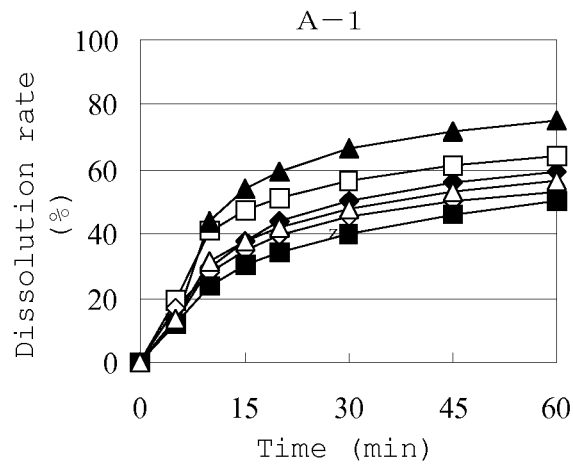
Figure 1B:
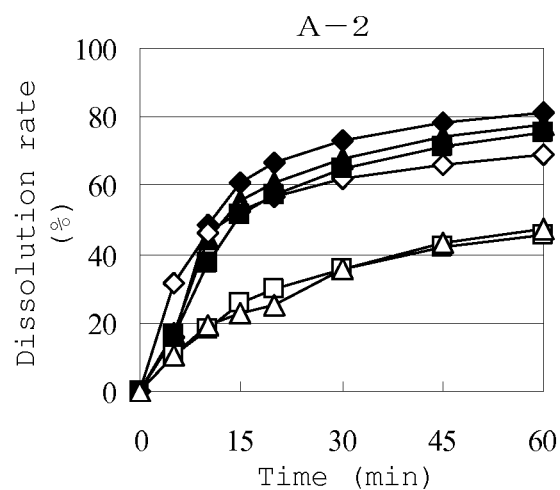

FIG. 1(b) is a graph showing the dissolution properties of compound I in a phosphate buffer of pH 6.8 for tablets (6 tablets per group) produced using granules granulated under granulation condition A and dried such that the water content of granules after drying was 2.0% or more to less than 4.0% (granulation condition A-2). The vertical axis shows dissolution rate (%), and the horizontal axis shows time (min).

Figure 1C:
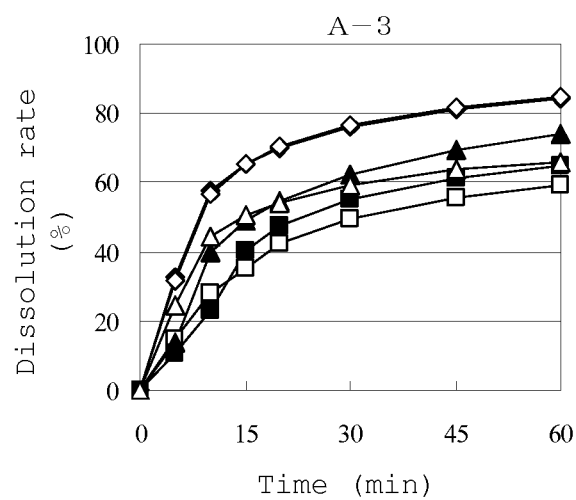

FIG. 1(c) is a graph showing the dissolution properties of compound I in a phosphate buffer of pH 6.8 for tablets (6 tablets per group) produced using granules granulated under granulation condition A and dried such that the water content of granules after drying was less than 2.0% (granulation condition A-3). The vertical axis shows dissolution rate (%), and the horizontal axis shows time (min).

Figure 2A:
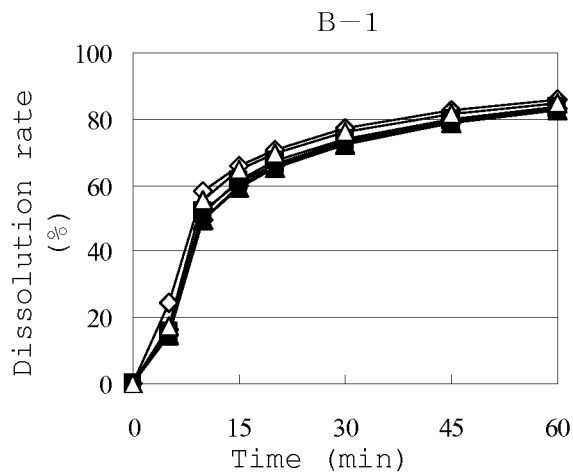

FIG. 2(a) is a graph showing the dissolution properties of compound I in a phosphate buffer of pH 6.8 for tablets (6 tablets per group) produced using granules granulated under granulation condition B and dried such that the water content of granules after drying was 4.0% or more (granulation condition B-1). The vertical axis shows dissolution rate (%), and the horizontal axis shows time (min).

Figure 2B:
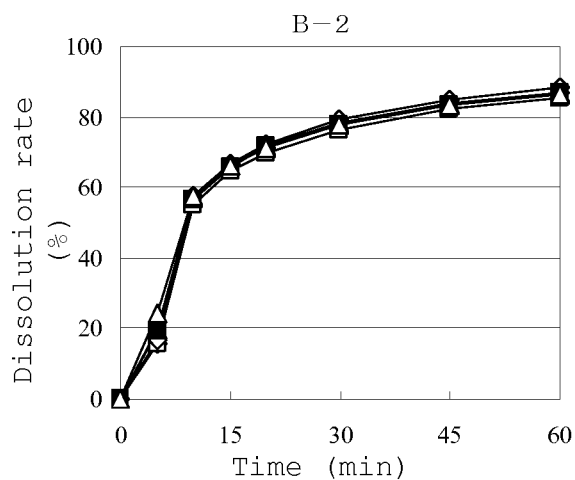

FIG. 2(b) is a graph showing the dissolution properties of compound I in a phosphate buffer of pH 6.8 for tablets (6 tablets per group) produced using granules granulated under granulation condition B and dried such that the water content of granules after drying was 2.0% or more to less than 4.0% (granulation condition B-2). The vertical axis shows dissolution rate (%), and the horizontal axis shows time (min).

Figure 2C:
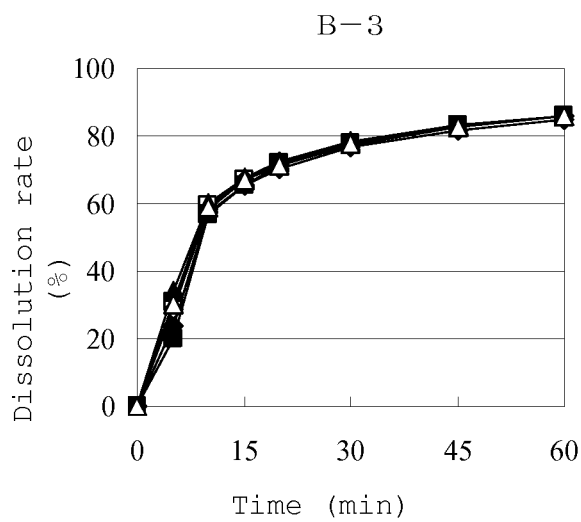

FIG. 2(c) is a graph showing the dissolution properties of compound I in a phosphate buffer of pH 6.8 for tablets (6 tablets per group) produced using granules granulated under granulation condition B and dried such that the water content of granules after drying was less than 2.0% (granulation condition B-3). The vertical axis shows dissolution rate (%), and the horizontal axis shows time (min).

Figure 3:
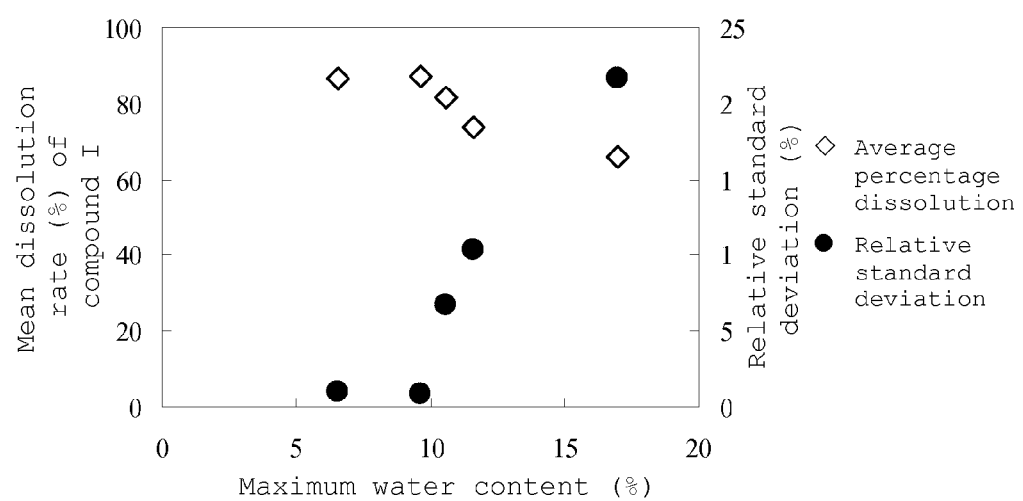

FIG. 3 is a diagram showing the relationship between the maximum water content of granules during granulation and the dissolution rate of compound I in a phosphate buffer of pH 6.8 or its variation (relative standard deviation) for a film-coated tablet containing 30 mg of compound I. The left vertical axis shows the dissolution rate (%) of compound I (average of 6 tablets per granulation condition) after 60 minutes from the start of the dissolution test in the buffer. The right vertical axis shows the relative standard deviation (%) of the dissolution rate of compound I (6 tablets per granulation condition) after 60 minutes into the dissolution test. The horizontal axis shows the maximum water content (%) of the granules during granulation.

DETAILED DESCRIPTION $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide represented by the following formula (I) (compound I):

[Formula 3]

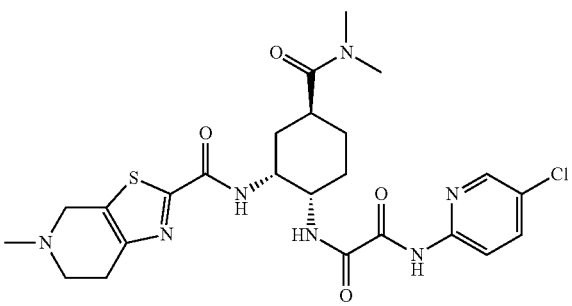

(I)

is called edoxaban (N-(5-chloropyridin-2-yl)-N'-[(1S,2R,4S)-4-(N,N-dimethylcarbamoyl)-2-(5-methyl-4,5,6,7-tetrahydro[1,3]thiazolo[5,4-c]pyridine-2-carboxamido)cyclohexyl]oxamide) as International Nonproprietary Name (INN).

Compound I may be a solvate (including hydrates) or may be a pharmaceutically acceptable salt or a solvate (including hydrates) of the salt.

Examples of the salt of compound I include hydrochloride, sulfate, hydrobromide, citrate, hydroiodide, phosphate, nitrate, benzoate, methanesulfonate, benzenesulfonate, 2-hydroxyethanesulfonate, p-toluenesulfonate, acetate, propionate, oxalate, malonate, succinate, glutarate, adipate, tartrate, maleate, fumarate, malate, and mandelate.

The salt of compound I is preferably hydrochloride, tartrate, methanesulfonate, or p-toluenesulfonate, particularly preferably p-toluenesulfonate.

Preferable examples of compound I or a pharmaceutically acceptable salt thereof, or a solvate thereof can include the following compounds:

$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl) ethanediamide;

$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl) ethanediamide hydrochloride;

$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl) ethanediamide p-toluenesulfonate; and $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl) ethanediamide p-toluenesulfonate monohydrate represented by the following formula (Ia) (compound Ia):

[Formula 4]

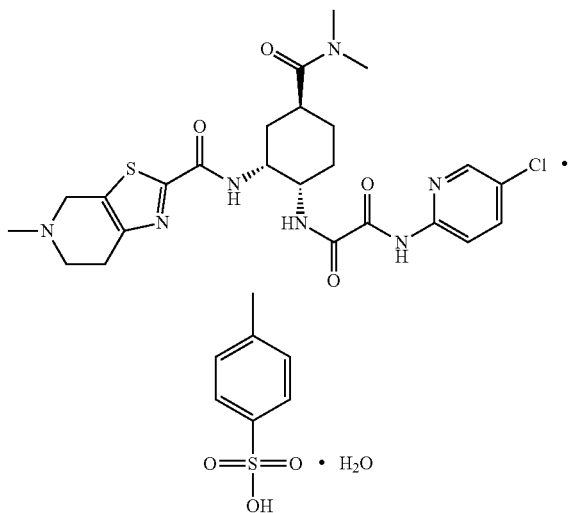

(Ia)

Compound Ia is called Edoxaban Tosilate Hydrate (written in English) as Japanese Accepted Names for Pharmaceuticals (JAN).

The compound I or a pharmaceutically acceptable salt thereof, or a solvate thereof (e.g., compound Ia) can be produced by a method described in any of Patent Documents 1 to 9 or a method equivalent thereto.

The efficacy and safety of pharmaceutical compositions for oral administration such as tablets or capsules are largely influenced by the dissolution properties of the active ingredient(s). Thus, the criteria regarding the dissolution properties are defined in each country. For example, in Japan, the USA, and Europe, the pharmacopoeia specifies a method for a dissolution test. In the dissolution test, various dissolution media (hereinafter, also referred to as test solutions or eluting solutions) are used. These dissolution media are adjusted to a pH range of 1 to 8. For example, strongly acidic dissolution media (e.g., JP 1st fluid described in the Japanese Pharmacopoeia and 0.1 N hydrochloric acid solutions), dissolution media of pH 3 to 5 (e.g., acetic acid-sodium acetate buffers and McIlvaine buffer), dissolution media of pH 6.8 (e.g., JP 2nd fluid described in the Japanese Pharmacopoeia and phosphate buffers of pH 6.8), and water are shown as the dissolution media specified by the pharmacopoeia or the like of each country. Preparations for oral administration are required to have favorable dissolution properties in dissolution tests using these dissolution media.

Compound I is a basic compound that exhibits favorable solubility in a strongly acidic aqueous solution, but reduced solubility in a neutral aqueous solution (neutral buffer, etc.). One of the features of the present invention is to granulate compound I, etc., an excipient, a disintegrant, and a binder with a maximum water content of the granules during granulation adjusted to 10% or less (preferably 10% or less, 9% or less, 8% or less, 7% or less, 6% or less, or 5% or less) to thereby drastically improve the dissolution rate of compound I, etc. from a pharmaceutical composition obtained using the granules and also improve the variation in dissolution among pharmaceutical compositions (e.g., tablets). Examples of the minimum water content of the granules include, but are not particularly limited to, 0%, 0.1%, 0.5%, 1%, 2%, and 3%.

In the present specification, the "granules during granulation" means a mixture in which compound I, etc., an excipient, and other appropriate additives are mixed at the start of the granulation step, and the mixture and/or granules obtained from the start of the granulation step to the completion of the granulation step.

In the present specification, the "maximum water content (%) of the granules during granulation" refers to the largest value of a water content (%) of the mixture and/or granules (including the mixture at the start of granulation) obtained from the mixing of the principal drug compound I, etc., an excipient, and other appropriate additives to the completion of granulation. In this context, the "water content (%) of the granules" is the value measured by a loss on drying method. For example, the water content (%) of the granules can be calculated by evaporating water from collected granules by heating and determining the proportion of the amount of water evaporated by this heating to 1 g of the collected granules. For example, when the collected granules are m (g) and become n (g) by heating, water is m−n (g) and the water content (%) of the granules can be calculated according to (m−n)/m×100.

In the present specification, the "step of granulating components under conditions for keeping the maximum water content of the granules during granulation at 10% or less" refers to performing granulation using a mixture containing compound I, etc., an excipient, and other appropriate additives while adjusting the granulation condition such that the maximum water content of the mixture and/or granules is kept at 10% or less from the start to completion of the granulation, for example, as described later, while adjusting the granulation condition with sampling from a granulator such that the water content of the mixture and/or granules sampled from the granulator is kept at 10% or less. Each parameter (e.g., inlet air temperature, spray speed, spray air pressure, or the inlet air volume) of a granulator for keeping the maximum water content of the granules during granulation at 10% or less can vary depending on the apparatus and environment in which the granulation is performed. As described later, those skilled in the pharmaceutical field, for the condition that the "maximum water content of the granules during granulation is kept at 10% or less", can easily set each parameter condition of each granulator so as to achieve the condition in the granulator and granulation environment.

The water content (%) of the granules can be measured in any stage at the start of granulation, during granulation, and at the completion of granulation. In order to measure the water content (%) of the granules at some midpoint during granulation, the granules may be collected by interruption of the granulation operation and can be collected, for example, via a sampling port, if any, in the granulator. In the case where from the water content (%) of the granules measured in some stage of granulation, it is expected that the continuation of granulation with the granulation condition unchanged results in a granule water content (%) exceeding 10%, those skilled in the art can adjust the maximum water content (%) of the granules so as not to exceed 10% by adjusting each condition (e.g., inlet air temperature, spray speed, spray air pressure, or the inlet air volume for fluidized-bed granulation, or the amount of water added for high-speed stirring granulation) influencing the water content of the granules. Thus, those skilled in the art, if not provided with each parameter (e.g., inlet air temperature, spray speed, spray air pressure, or the inlet air volume) of a granulator as the "conditions for keeping the maximum water content (%) of the granules during granulation at 10% or less", can set each parameter (e.g., inlet air temperature, spray speed, spray air pressure, or the inlet air volume) suitable for the granulator used with the maximum water content (%) of the granules during granulation as an index and can thereby carry out the present invention. The aforementioned setting of each parameter (e.g., inlet air temperature, spray speed, spray air pressure, or the inlet air volume) of a granulator by sampling may be performed every time granulation is carried out, or may be performed at least once. It is understood that once those skilled in the pharmaceutical field find each parameter (e.g., inlet air temperature, spray speed, spray air pressure, or the inlet air volume) that keeps the maximum water content of the granules during granulation at 10% or less in the granulator used, they can use this set value in the next granulation to carry out the granulation step without sampling.

Examples of a granulation method include wet granulation. Examples of the wet granulation method include fluidized-bed granulation and high-speed stirring granulation and preferably include fluidized-bed granulation.

In the case of fluidized-bed granulation, compound I, etc., an excipient, a disintegrant, and so on are mixed, and the mixture can be granulated by spraying thereto an aqueous binder solution. Each parameter, for example, inlet air temperature, spray speed, spray air pressure, or the inlet air volume, of a granulator can be set appropriately by those skilled in the art depending on the granulator used with the maximum water content (%) of the granules during granulation as an index. For example, when granulation is performed at a laboratory level (e.g., 5-kg scale) (fluidized-bed granulator FLO-5 (manufactured by Freund Corp.)), the inlet air temperature can be set to approximately 70° C. to 90° C.; the spray speed can be set to 30 mL/min to 60 mL/min; and the spray air pressure can be set to 0.15 to 0.30 MPa. Alternatively, when granulation is performed at a commercial scale production level (e.g., 100-kg scale) (WSG-120 (manufactured by Powrex Corp.)), the inlet air temperature can be set to approximately 70° C. to 90° C.; the spray speed can be set to 600 mL/min to 800 mL/min; the spray air volume can be set to 600 to 850 NL/min.

In the case of high-speed stirring granulation, purified water is added to compound I, etc., an excipient, a disintegrant, a binder, and so on with stirring using stirring blades, and the mixture can be granulated by kneading. Each parameter, for example, the addition rate of purified water, of a granulator can be set appropriately by those skilled in the art depending on the granulator used with the maximum water content (%) of the granules during granulation as an index.

The thus-obtained granules containing compound I, etc. are subsequently subjected to a drying step, if necessary. No particular limitation is imposed on the drying step, so long as the granules are dried until the final water content (dry weight method) is 1.0% to 5.0%. For example, the drying temperature is room temperature to 100° C., preferably 80° C. to 90° C., and the drying time is several tens of minutes to several hours, preferably on the order of 10 minutes to 30 minutes.

The obtained granules are sieved, if necessary, and may then be used in a pharmaceutical composition in the dosage form of granules or a powder, or in the form of a tablet by blending with a lubricant, or in the form of a capsule by encapsulation. No particular limitation is imposed on the dosage form of the pharmaceutical composition of the present invention, so long as the preparation thereof can be orally administered to a subject. However, the dosage form is preferably a solid preparation, more preferably a tablet, granules, a powder (including fine granules), or a capsule, even more preferably a tablet. The solid preparation may be produced through a widely known production method. In one exemplified procedure, the pharmaceutical composition of the present invention is prepared through mixing compound I or a pharmaceutically acceptable salt thereof, or a solvate thereof, a sugar alcohol and/or a water-swelling additive, and optional additives such as a disintegrant, a binder, a fluidizing agent, a lubricant, a coloring agent, and a polishing agent, and the mixture is processed through, for example, the method of producing solid preparations described in the general rules for preparations in the Japanese Pharmacopeia.

Moreover, when the pharmaceutical composition of the present invention is in the dosage form of a tablet, tablets may be produced through compression of the granules obtained as described above. The pressure of compression may be determined within an appropriate range, so long as the effect of the present invention is not impaired. The pressure is preferably 5 to 15 kN. Moreover, the shape of the tablet is not particularly limited, preferably a lens, disc, round, oval (e.g., caplets), a tear shape, or a polygonal (e.g., triangle or rhombus) shape. Furthermore, the produced tablet may be further coated with a coating agent by means of a pan coater through spraying a suspension/solution of the coating agent.

When the pharmaceutical composition of the present invention is in the dosage form of granules, for example, the granules obtained as described above may be used directly or may be granulated into the desired particle shape through an appropriate technique. Additionally, the thus-produced granules may be coated with a coating agent through spraying a suspension/solution of the coating agent.

Alternatively, when the pharmaceutical composition of the present invention is in the dosage form of a powder, for example, the desired powder or microparticles may be produced from the granules obtained as described above through an appropriate technique. Additionally, the thus-produced powder or microparticles may be coated with a coating agent through spraying a suspension/solution of the coating agent.

Alternatively, when the pharmaceutical composition of the present invention is in the dosage form of a capsule, the aforementioned granules or powders may be encapsulated with coating capsules.

Excipients used in the production of a solid preparation such as a tablet are not particularly limited, and excipients usually used by those skilled in the art can be used.

Preferable examples of the excipients include a sugar alcohol, a water-swelling additive, and their combination.

The water-swelling additive employed in the present invention means an additive for pharmaceuticals which swells with water added thereto. Examples of the water-swelling additive in the present invention include excipients and bases having water swellability. Specific examples of the water-swelling additive include pregelatinized starch, gelatinized starch, crystalline cellulose, sodium carboxymethyl starch, carmellose (carboxymethyl cellulose), carmellose calcium, croscarmellose sodium (croscarboxymethyl cellulose sodium), soybean lecithin, low-substituted hydroxypropyl cellulose, tragacanth powder, and bentonite. These water-swelling additives may be employed singly or in combination of two or more types.

Among these water-swelling additives, pregelatinized starch and crystalline cellulose are preferred, with pregelatinized starch being more preferable. As crystalline cellulose, Ceolus (manufactured by Asahi Kasei Corp.) is particularly preferred. As the pregelatinized starch, PCS (manufactured by Asahi Kasei Corp.) or Starch 1500 (manufactured by Colorcon Japan Ltd.) is particularly preferred.

The sugar alcohol that can improve the solubility of compound I, etc. is preferably mannitol, erythritol, or xylitol, or the like, particularly preferably mannitol.

To the composition of the present invention, a water-soluble excipient other than sugar alcohols may be added. Examples of the water-soluble excipient include: fructose, purified sucrose, sucrose, purified sucrose spherical granules, lactose, anhydrous lactose, sucrose-starch spherical granules, semi-digested starch, glucose, glucose hydrate, powder sugar, pullulan, and β-Cyclodextrin. Other than saccharides, examples further include aminoethylsulfonic acid, maltose syrup powder, sodium chloride, citric acid, sodium citrate, glycine, calcium gluconate, L-glutamine, tartaric acid, potassium hydrogentartrate, ammonium carbonate, dextran 40, dextrin, calcium lactate, povidone, Macrogol (polyethylene glycol) 1500, Macrogol 1540, Macrogol 4000, Macrogol 6000, anhydrous citric acid, DL-malic acid, sodium hydrogen phosphate, potassium dihydrogenphosphate, and sodium dihydrogenphosphate.

The water-soluble excipient is preferably selected from saccharides. Specific examples include purified sucrose, sucrose, lactose, lactose granules, glucose, glucose hydrate, powder sugar, or pullulan. Of these, lactose is even more preferred.

The solid preparation containing compound I, etc. preferably contains a sugar alcohol in an amount of 0.01 to 99.0 wt. %, preferably 20 to 80 wt. %, more preferably 40 to 60 wt. %, in terms of the effect of improving the dissolution properties of compound I, etc. Also, the solid preparation containing compound I, etc. preferably contains a water-swelling additive in an amount of 0.01 to 90 wt. %, preferably 0.1 to 80 wt. %, more preferably 5 to 50 wt. %.

In the case where the preparation contains the aforementioned water-swelling additive and sugar alcohol, the ratio of water-swelling additive to sugar alcohol in the preparation is preferably, to 1 part by weight (water-swelling additive), 0.05 to 50 parts by weight (sugar alcohol), more preferably 1 to 10 parts by weight (sugar alcohol), particularly preferably 1.5 to 4 parts by weight (sugar alcohol).

In addition to the combination of aforementioned sugar alcohol and water-swelling additive, the pharmaceutical composition containing compound I etc. may further contain a water-insoluble excipient, a disintegrant, a binder, a fluidizing agent, a lubricant, a coloring agent, a polishing agent, etc., so long as the effects of the present invention are not impaired.

Examples of the water-insoluble excipient include L-aspartic acid, alginic acid, carmellose sodium, hydrous silicon dioxide, crospovidone, calcium glycerophosphate, magnesium silicate aluminate, calcium silicate, magnesium silicate, light anhydrous silicic acid, crystalline cellulose, cellulose powder, synthetic aluminum silicate, synthetic aluminum silicate/hydroxypropyl starch/crystalline cellulose, flour, wheat starch, wheat germ flour, wheat germ oil, rice powder, rice starch, cellulose acetate phthalate, titanium oxide, magnesium oxide, dihydroxyaluminum aminoacetate, calcium tertiary phosphate, talc, calcium carbonate, magnesium carbonate, precipitated calcium carbonate, natural aluminum silicate, corn starch, granulated corn starch, potato starch, hydroxypropyl cellulose, hydroxypropyl starch, calcium hydrogenphosphate anhydrous, granulated calcium hydrogenphosphate anhydrous, or calcium dihydrogenphosphate. Of these, crystalline cellulose or cellulose powder is preferred as a water-insoluble excipient.

Examples of the disintegrant include adipic acid, alginic acid, gelatinized starch, sodium carboxymethyl starch, carmellose, carmellose calcium, carmellose sodium, hydrous silicon dioxide, calcium citrate, croscarmellose sodium, crospovidone, light anhydrous silicic acid, crystalline cellulose, synthetic aluminum silicate, wheat starch, rice starch, cellulose acetate phthalate, calcium stearate, low-substituted hydroxypropyl cellulose, corn starch, tragacanth powder, potato starch, hydroxyethylmethyl cellulose, hydroxypropyl starch, pregelatinized starch, monosodium fumarate, povidone, anhydrous citric acid, methyl cellulose, or calcium dihydrogenphosphate. Of these, crospovidone or sodium carboxymethyl starch is preferred as a disintegrant.

Examples of the binder include maltose syrup powder, gum arabic, gum arabic powder, sodium alginate, propylene glycol alginate ester, hydrolyzed gelatin powder, hydrolyzed starch-light anhydrous silicic acid, fructose, carboxyvinyl polymer, carboxymethylethyl cellulose, hydrous silicon dioxide, agar powder, light anhydrous silicic acid, light anhydrous silicic acid-containing hydroxypropyl cellulose, crystalline cellulose, synthetic aluminum silicate, high-molecular polyvinylpyrrolidone, copolydone, wheat flour, wheat starch, rice flour, rice starch, polyvinyl acetate resin, cellulose acetate phthalate, dioctyl sodium sulfosuccinate, dihydroxyaluminum aminoacetate, sodium potassium tartrate, water, sucrose fatty acid ester, purified gelatin, purified sucrose, gelatin, D-sorbitol, dextrin, starch, corn starch, tragacanth, tragacanth powder, lactose, concentrated glycerin, sucrose, potato starch, hydroxyethylcellulose, hydroxyethylmethyl cellulose, hydroxypropyl cellulose, hydroxypropyl starch, hydroxypropylmethyl cellulose 2208, hydroxypropylmethyl cellulose 2906, hydroxypropylmethyl cellulose 2910, hydroxypropylmethyl cellulose phthalate, vinylpyrrolidone-vinyl acetate copolymers, piperonyl butoxide, glucose, pregelatinized starch, fumaric acid, fumaric acid-stearic acid-polyvinyl acetal diethylaminoacetate-hydroxypropylmethyl cellulose 2910 mixtures, pullulan, povidone, polyvinyl alcohol (completely saponified product), polyvinyl alcohol (partially saponified product), sodium polyphosphate, Macrogol 4000, Macrogol 6000, Macrogol 20000, D-mannitol, or methylcellulose.

Examples of the fluidizing agent include hydrous silicon dioxide, light anhydrous silicic acid, crystalline cellulose, synthetic aluminum silicate, titanium oxide, stearic acid, calcium stearate, magnesium stearate, calcium tertiary phosphate, talc, corn starch, or magnesium aluminometasilicate.

Examples of the lubricant include cocoa fat, carnauba wax, hydrous silicon dioxide, dry aluminum hydroxide gel, glycerin fatty acid ester, magnesium silicate, light anhydrous silicic acid, crystalline cellulose, hardened oil, synthetic aluminum silicate, white beeswax, magnesium oxide, sodium potassium tartrate, sucrose fatty acid ester, stearic acid, calcium stearate, magnesium stearate, stearyl alcohol, polyoxyl 40 stearate, cetanol, soybean hardened oil, gelatin, talc, magnesium carbonate, precipitated calcium carbonate, corn starch, potato starch, fumaric acid, stearyl sodium fumarate, Macrogol 600, Macrogol 4000, Macrogol 6000, beeswax, magnesium metasilicate aluminate, sodium laurate, or magnesium sulfate.

Examples of the coloring agent can include yellow iron sesquioxide, iron sesquioxide, titanium oxide, orange essence, brown iron oxide, β-carotene, black iron oxide, food blue No. 1, food blue No. 2, food red No. 2, food red No. 3, food red No. 102, food yellow No. 4, and food yellow No. 5.

Examples of the polishing agent include carnauba wax, hardened oil, a polyvinyl acetate resin, white beeswax, titanium dioxide, stearic acid, calcium stearate, polyoxyl 40 stearate, magnesium stearate, purified shellac, purified paraffin/carnauba wax mixture, cetanol, talc, colored silver foil, white shellac, paraffin, povidone, Macrogol 1500, Macrogol 4000, Macrogol 6000, beeswax, glycerin monostearate, or rosin. Of these, carnauba wax, titanium dioxide, or talc is particularly preferred as a polishing agent.

The present invention also relates to a coated pharmaceutical composition for oral administration containing compound I, etc. granulated as described above.

The pharmaceutical composition for oral administration of the present invention containing compound I, etc. granulated as described above and a coating agent is not limited to coated solid preparations such as coated tablets and encompasses various solid preparations comprising coating agents. For example, a solid preparation containing compound I, etc., wherein coating agents are formulated in a matrix form in the solid preparation is also included in the present invention.

Examples of the coating agents used for promoting the dissolution properties of compound I, etc. in this pharmaceutical composition for oral administration can include coating agents generally employed in pharmaceutical manufacturing for coating tablets and granules therewith. Preferably, the coating agent has low solubility within the pH range in the intestine. Specifically, a coating agent which is difficult to dissolve within the pH range in the intestine is generally preferred, as compared with an enteric coating agent.

Specific examples of the preferred coating agents include the following:
(1) cellulose derivatives such as hypromellose (hydroxypropyl methylcellulose), hydroxypropyl cellulose, ethyl cellulose, and methyl cellulose;
(2) polyvinyl compounds such as polyvinyl alcohol, povidone (polyvinylpyrrolidone), polyvinyl acetal diethylaminoacetate, and a polyvinyl acetate resin;
(3) acrylate derivatives such as an aminoalkyl methacrylate copolymer RS and an ethyl acrylate-methyl methacrylate copolymer dispersion; and
(4) saccharides (including sugar alcohols) such as sucrose and mannitol, which are used as sugar coating agents. These coating agents may be used singly or in combination of two or more types. Hypromellose or a hypromellose-based coating agent includes types such as hypromellose 2208, hypromellose 2906, and hypromellose 2910 having different viscosities (mPa s). These types having different viscosities may be used singly or in combination of two or more types.

Among these, preferred are one or more types selected from the group consisting of cellulose derivatives (hypromellose, methyl cellulose, ethyl cellulose, methyl cellulose, or hydroxypropyl cellulose); polyvinyl compounds (polyvinyl alcohol, povidone, polyvinyl acetate resin, or polyvinyl acetal diethylaminoacetate); acrylate derivatives (amino alkyl methacrylate copolymer RS and ethyl acrylate-methyl methacrylate copolymer dispersion); and saccharides (including sugar alcohols) (sucrose and mannitol).

Of these, one or more types selected from among cellulose derivatives and polyvinyl compounds are more preferred. Still more preferred are one or more types selected from among hypromellose, ethyl cellulose, and polyvinyl alcohol. Among them, hypromellose is particularly preferred.

In the present invention, the aforementioned coating agent and other additives required for preparing a coating suspension (e.g., a plasticizer) may be incorporated in combination into the composition. Examples of the additives required for preparing a coating suspension (e.g., plasticizer) include Macrogols (polyethylene glycols having an average molecular weight of 1,000 to 35,000) such as Macrogol 1000, Macrogol 1500, Macrogol 1540, Macrogol 4000, Macrogol 6000, Macrogol 8000, Macrogol 20000, and Macrogol 35000; glycerin fatty acid ester; sucrose fatty acid ester; castor oil; triethyl citrate; triacetin; or talc. The aforementioned coating agents may further contain the below-mentioned coloring agent, and the mixture may be incorporated into the pharmaceutical composition of the present invention.

The pharmaceutical composition of the present invention contains 0.5 to 20% by weight, preferably 1 to 15% by weight, more preferably 1.5 to 10% by weight of the coating agents in terms of the effect of promoting the dissolution of compound I, etc.

In the present invention, the solid preparation containing compound I etc. may be coated with the aforementioned coating agent through a widely known coating process for solid preparation coating. No particular limitation is imposed on the coating process, and for example, there may be employed a spray coating process in which a solution/dispersion of the coating agent is sprayed onto a solid preparation containing compound I etc. by means of a fluidized bed coater or a pan coater, a dip coating process in which a solid preparation containing compound I etc. is dipped in a coating suspension; and a dry coating process employing impact in a gas flow. A solid preparation containing compound I etc. which has not been subjected to the coating process may be produced through a conventionally known process.

Thus, the pharmaceutical composition of the present invention may be produced by preparing a solid preparation containing compound I, etc. as a pharmaceutically active ingredient through a known method and then coating the thus prepared solid preparation with a coating agent.

The dose of the pharmaceutical composition comprising the compound of the present invention or the pharmaceutically acceptable salt thereof, or the solvate thereof as an active ingredient is not particularly limited and can be selected appropriately according to various conditions such as the age, body weight, and symptoms of a patient. The pharmaceutical composition is preferably administered once to several times a day, preferably once to twice a day, at a dose of 1 mg to 1000 mg, preferably 5 mg to 500 mg, more preferably 5 mg to 300 mg, even more preferably 5 mg to 100 mg of the active ingredient per day in an adult according to the symptoms.

The amount of compound I contained in one unit of the pharmaceutical composition (e.g., tablet or capsule) is usually 1 to 100 mg, preferably 5 to 75 mg, more preferably 5 to 60 mg, in terms of the free form of compound I.

The dissolution properties of compound I, etc. of the pharmaceutical composition of the present invention can be evaluated by, for example, dissolution tests disclosed in the Japanese Pharmacopoeia, the United States Pharmacopoeia (USP), and the European Pharmacopoeia. Examples of the test medium employed in the dissolution tests will be described.

Non-limiting examples of the aforementioned strongly acidic dissolution medium include the JP 1st fluid described in the Japanese Pharmacopoeia; and "USP 0.1N HCl, Simulated Gastric Fluid without Enzyme" described in the United States Pharmacopoeia.

Non-limiting examples of the dissolution medium (pH 6.8) include the JP 2nd fluid and phosphate buffer (pH 6.8) described in the Japanese Pharmacopoeia, "USP Phosphate Buffer (pH 6.8)", Simulated Intestinal Fluid without Enzyme described in the United States Pharmacopoeia, and Phosphate Buffer Solution (pH 6.8) described in the European Pharmacopoeia.

Moreover, dissolution media (pH 3 to 5) may be a test medium having a pH 4.0 or pH 4.5. Specific examples include acetic acid-sodium acetate buffer described in the Japanese Pharmacopoeia, "USP Acetate Buffer" described in the United States Pharmacopoeia, and Acetate Buffer Solution (pH 4.5) described in the European Pharmacopoeia. Moreover, a diluted McIlvaine buffer of pH 4.0 may also be used. However, the dissolution medium of pH 3 to 5 is not limited to the above examples.

These dissolution media are prepared through methods described in the corresponding pharmacopoeia or the like of each country. When the employed dissolution medium is a buffer solution, variation of the pH of the test medium is preferably within ±0.05 of the pH defined for each dissolution medium.

When the tablet containing compound I, etc. granulated using the method of the present invention was subjected to a dissolution test by the paddle method at a rotation speed of 50 rpm, the tablet exhibited an mean dissolution rate, in a dissolution medium having a pH of 6.8, of 60% or higher in 30 minutes after the start of the dissolution test and 70% or higher in 60 minutes after the start, and had no variation in dissolution behavior among tablets.

When the pharmaceutical composition of the present invention is subjected to the method described in the dissolution test method of the Japanese Pharmacopoeia (paddle method; at a rotation speed of 50 rpm), the composition exhibits an mean dissolution rate of the compound I, etc. in a dissolution medium having a pH of 6.8, preferably of 60% or higher in 30 minutes after the start of the dissolution test and 70% or higher in 60 minutes after the start, more preferably of 70% or higher in 30 minutes after the start and 80% or higher in 60 minutes after the start.

When the pharmaceutical composition of the present invention is subjected to the method described in the dissolution test method of the Japanese Pharmacopoeia (paddle method; at a rotation speed of 50 rpm), the composition exhibits an mean dissolution rate of the compound I, etc. in a dissolution medium having a pH of 4.5, preferably of 85% or higher in 30 minutes after the start of the dissolution test.

As used herein, the "mean dissolution rate" refers to the average of percentage dissolution values obtained from at least 3, preferably 6, more preferably 12 solid preparation samples for each type of solid preparation.

The pharmaceutical composition of the present invention exhibits a high inhibitory effect on activated blood coagulation factor X (FXa) and as such, is useful as an anticoagulant agent or an agent for preventing and/or treating thrombosis or embolism. The pharmaceutical composition of the present invention is useful as a pharmaceutical drug for mammals including humans, an activated blood coagulation factor Xa inhibitor, an anticoagulant agent, an agent for preventing and/or treating thrombosis or embolism, an agent for preventing and/or treating thrombotic diseases, and further, an agent for preventing (in the present specification, prevention includes secondary prevention) and/or treating, for example, cerebral infarction, cerebral embolism, myocardial infarction, angina pectoris, unstable angina, acute coronary syndrome (ACS), pulmonary infarction, pulmonary embolism, thromboembolism or attack accompanying nonvalvular atrial fibrillation (NVAF), deep vein thrombosis, disseminated intravascular coagulation syndrome, thrombosis after prosthetic valve/joint replacement, thromboembolism after total hip replacement (THR), thrombosis and/or reocclusion after revascularization, thrombosis at the time of extracorporeal circulation, blood coagulation at the time of blood collection, Buerger's disease, thromboembolism accompanying systemic inflammatory response syndrome (SIRS), or thromboembolism accompanying multiple organ dysfunction syndrome (MODS).

Next, the present invention will be described in detail with reference to the Examples. However, the present invention is not intended to be limited to these by any means.

EXAMPLES

Granules containing $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide p-toluenesulfonate monohydrate (hereinafter, referred to as compound Ia) were prepared with varying maximum water contents of the granules during granulation and/or varying drying conditions after granulation. Tablets containing compound Ia were produced using the granules. Each tablet thus obtained was examined for dissolution properties at 50 rpm by the second method of the dissolution test (paddle method) described in the Japanese Pharmacopoeia. The dissolution amount was calculated as the mean dissolution rate of 6 tablets. The dissolution medium used was 900 mL of phosphate buffer of pH 6.8 (USP Phosphate buffer (pH 6.8)).

Example 1

Granulation

Under each condition described in Table 1, 1010 g of compound Ia, 2480 g of sieved mannitol (Mannit P, manufactured by TOWA-KASEI Co., Ltd.), 1050 g of pregelatinized starch (PCS PC-10, manufactured by Asahi Kasei Chemicals Corp.), and 267.5 g of crospovidone (Polyplasdone INF-10, manufactured by ISP) were subjected to fluidized-bed granulation using 2179 mL of an aqueous solution containing 7 w/v % hydroxypropyl cellulose (HPC-L, manufactured by Nippon Soda Co., Ltd.). In the fluidized-bed granulation, a fluidized-bed granulator (FLO-5, manufactured by Freund Corp.) was used.

TABLE 1

|  | Granulation condition A: high moisturization water condition | Granulation condition B: low moisturization water condition |
|---|---|---|
| Inlet air set temperature | Initial: 65° C., 10 minutes or later after start: 80° C. | 85° C. |
| Liquid spray speed | 50 mL/min | 50 mL/min |
| Spray air pressure | 0.15 MPa | 0.20 MPa |

(Drying)

Next, the granules thus granulated under each condition were dried such that the water content of granules after drying was 4.0% or more (A-1 and B-1 in Table 2), 2.0% or more and less than 4.0% (A-2 and B-2 in Table 2), or less than 2.0% (A-3 and B-3 in Table 2).

TABLE 2

| | Granulation condition A: high moisturization water condition | | | Granulation condition B: low moisturization water condition | | |
|---|---|---|---|---|---|---|
| | A-1 | A-2 | A-3 | B-1 | B-2 | B-3 |
| Water content of granules after drying | 4.0% or more | 2.0% or more and less than 4.0% | less than 2.0% | 4.0% or more | 2.0% or more and less than 4.0% | less than 2.0% |

(Compression)

198.4 g of the granules thus granulated and dried under each condition was mixed with 1.6 g of magnesium stearate (HyQual Code 5712, manufactured by Tyco Healthcare), and the mixture was compressed into tablets using a single-punch tableting machine (8.5 mmφ, 7R, tablet thickness: 4.2 mm, 200 mg/tablet). Subsequently, these tablets were each film-coated with a 12 w/v % suspension of a coating agent (OPADRY (registered trademark) 03F42132) composed mainly of hypromellose using a pan coater (High Coater Mini, manufactured by Freund Corp.) such that the amount of coating was 10 mg in each tablet. The amount of each component per tablet is shown in Table 3 below.

TABLE 3

| Component | Amount (mg) |
|---|---|
| Compound Ia | 40.41 |
| (in terms of compound I) | (30.00) |
| D-mannitol | 99.19 |
| Pregelatinized starch | 42.00 |
| Crospovidone | 10.70 |
| Hydroxypropyl cellulose | 6.100 |
| Magnesium stearate | 1.600 |
| Coating agent | 10.00 |
| Total weight of tablet | 210.0 |

(Results)

The physical properties of the granules and the tablets prepared under varying granulation conditions and drying conditions are shown in Table 4.

example, the proportion of the granules passing through a 140 or finer mesh was 27.9 to 28.8% in the granulation condition A groups and 39.5 to 41.9% in the granulation condition B groups. The hardness of the film-coated tablet was a slightly higher value exhibited by the granulation condition B groups than the granulation condition A groups and was, for example, 11.5 to 13.3 kp in the granulation condition A groups and 12.3 to 15.1 kp in the granulation condition B groups. These physical properties of the granules and the tablets did not largely differ under the same granulation conditions.

The dissolution of compound I from each tablet in phosphate buffer of pH 6.8 is shown in FIGS. 1 and 2. Each graph in FIGS. 1 and 2 shows results of measuring the amount of compound I dissolved in the phosphate buffer of pH 6.8. The vertical axis shows the dissolution rate of compound I, and the horizontal axis shows time (min).

As a result, the reduction in dissolution amount, the reduction in dissolution rate, or the variation in dissolution behavior was not observed in the granulation condition B groups (FIGS. 2(a)-2(c)), whereas the reduction in dissolution amount and in dissolution rate and the variation in dissolution behavior were observed in the granulation condition A groups (FIGS. 1(a)-1(c)). By contrast, tablets prepared by compression from the granules of the granulation condition A groups after size selection equivalent to the particle sizes of the granulation condition B groups by sieving and pulverization still exhibited the reduction in dissolution rate and the variation in dissolution behavior, suggesting that the particle size of granules did not influence

TABLE 4

| | | A: High moisturization water condition | | | B: Low moisturization water condition | | |
|---|---|---|---|---|---|---|---|
| | | A-1 | A-2 | A-3 | B-1 | B-2 | B-3 |
| Maximum water content (%) of granules during granulation | | 17.0 | | | 6.6 | | |
| Water content (%) of granules after drying | | 4.3 | 2.9 | 1.7 | 4.0 | 2.6 | 1.4 |
| Particle size distribution (%) | -30 mesh | 0.5 | 0.5 | 0.6 | 0 | 0 | 0 |
| | 30-42 mesh | 0.3 | 0.4 | 0.4 | 0 | 0 | 0 |
| | 42-60 mesh | 1.9 | 2.1 | 1.6 | 0.5 | 0.3 | 0.3 |
| | 60-83 mesh | 19.1 | 19.5 | 18.3 | 12.0 | 11.4 | 8.7 |
| | 83-100 mesh | 18.3 | 18.0 | 18.0 | 14.7 | 15.0 | 15.0 |
| | 100-140 mesh | 31.1 | 31.5 | 32.5 | 30.9 | 32.9 | 36.5 |
| | 140-200 mesh | 17.7 | 16.9 | 19.1 | 21.2 | 21.2 | 24.0 |
| | 200 mesh- | 11.1 | 11.0 | 9.6 | 20.7 | 19.2 | 15.5 |
| Average hardness (kp) of tablets | | 13.3 | 12.1 | 11.5 | 15.1 | 13.6 | 12.3 |

The maximum water content of granules was 17.0% for granulation condition A and 6.6% for granulation condition B. The particle size of the granules was finer in the granulation condition B groups (B-1, B-2, and B-3) than the granulation condition A groups (A-1, A-2, and A-3). For dissolution. It was also confirmed that the granulation condition B groups were insusceptible to their particle sizes.

Granulation condition A and granulation condition B were each studied for the influence of the difference in the water content of granules after drying on the dissolution of compound I from the tablets (A-1, A-2, and A-3 in FIGS. 1(a)-1(c) or B-1, B-2, and B-3 in FIGS. 2(a)-2(c) were compared). As a result, no large difference was observed under the same granulation conditions.

Example 2

The dissolution properties of compound I from each tablet were tested in phosphate buffer of pH 6.8 with varying maximum water contents of the granules during granulation. 7.274 kg of compound Ia, 17.85 kg of sieved mannitol (Mannit P, manufactured by TOWA-KASEI Co., Ltd.), 7.56 kg of pregelatinized starch (PCS PC-10, manufactured by Asahi Kasei Chemicals Corp.), and 1.926 kg of crospovidone (Polyplasdone INF-10, manufactured by ISP) were subjected to fluidized-bed granulation using 15.5 L of an aqueous solution containing 7 w/v % hydroxypropyl cellulose (HPC-L, manufactured by Nippon Soda Co., Ltd.). In the fluidized-bed granulation, a FLO-30 or FLO-30SJ (manufactured by Freund Corp.) was used. Inlet air set temperature, liquid spray speed, and spray air pressure were set to 90° C., 250 mL/min, and 0.25 MPa, respectively. As a result, the granules were successfully produced with a maximum water content of the granules during granulation of 9.6%. Furthermore, the granules were obtained with their formulation ratio unchanged from above at appropriately varying inlet air set temperature, liquid spray speed, and spray air pressure such that the maximum water content of the granules during the granulation step was 10.6% or 11.6%. 3 types of film-coated tablets were prepared in the same way as in Example 1 using the granules thus obtained under these 3 conditions, respectively.

These 3 types of tablets and 2 types of tablets obtained under granulation conditions A-2 and B-2 of Example 1 were subjected to the dissolution test in the phosphate buffer of pH 6.8. These were each plotted for the dissolution amount (mean dissolution rate of 6 tablets per granulation condition) after 60 minutes into the dissolution test and the relative standard deviation (6 tablets per granulation condition) of the dissolution rate after 60 minutes into the dissolution test (FIG. 3).

Example 3

20.2 kg of compound Ia, 49.6 kg of sieved mannitol (PEARITOL 50C, manufactured by Roquette Corp.), 21 kg of pregelatinized starch (PCS PC-10, manufactured by Asahi Kasei Chemicals Corp.), and 5.35 kg of crospovidone (Polyplasdone INF-10, manufactured by ISP) were subjected to fluidized-bed granulation using 43.57 kg of an aqueous solution containing 7 w/w % hydroxypropyl cellulose (HPC-L, manufactured by Nippon Soda Co., Ltd.). In the fluidized-bed granulation, a WSG-120 (manufactured by Powrex Corp.) was used. Inlet air temperature, liquid spray speed, and spray air volume were set to 90° C., 700 g/min, and 750 NL/min, respectively, such that the maximum water content (%) of the granules during granulation was 10% or less.

Four batches of the obtained granules were dried in the same way as in Example 1 and prepared into film-coated tablets. The obtained film-coated tablets were subjected to the dissolution test in the phosphate buffer of pH 6.8 in the same way as in Example 1.

As a result, even at a commercial scale production scale, the film-coated tablets produced using the granules granulated with the maximum water content (%) of the granules during granulation kept at 10% or less exhibited high dissolution properties (70% or more in 30 minutes after the start of the dissolution test and 80% or more in 60 minutes after the start) in the phosphate buffer of pH 6.8 and had no variation in dissolution behavior among tablets.

INDUSTRIAL APPLICABILITY

The present invention provides a pharmaceutical composition that exhibits favorable dissolution behavior in the neutral region and is useful as an agent for preventing and/or treating thrombosis or embolism, and a method for producing the same.

The invention claimed is:
1. A method for producing a pharmaceutical composition containing $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide represented by the following formula (I):

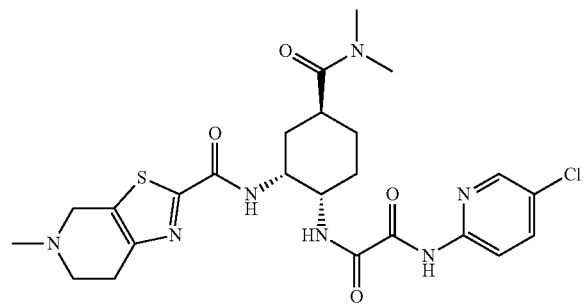

(I)

or a pharmaceutically acceptable salt thereof, the method comprising the step of wet-granulating
(A) a compound represented by formula (I) or a pharmaceutically acceptable salt thereof,
(B) one or more excipients selected from the group consisting of a sugar alcohol and a water-swelling additive,
wherein the sugar alcohol is mannitol, xylitol, or erythritol, the water-swelling additive is pregelatinized starch or crystalline cellulose,
(C) a disintegrant, wherein the disintegrant is crospovidone or sodium carboxymethyl starch, and
(D) a binder, to provide granules under conditions for keeping the maximum water content of the granules during granulation at 10% or less,
wherein said wet-granulating is fluidized-bed granulation, and the method further comprises the step of compressing the granules, wherein when the composition is subjected to a dissolution test by the paddle method at a rotation speed of 50 rpm, the composition exhibits a mean dissolution rate of the compound represented by formula (I), in a dissolution medium having a pH of 6.8, of 60% or higher in 30 minutes after the start of the dissolution test and 70% or higher in 60 minutes after the start.
2. The method according to claim 1, wherein the maximum water content of the granules during granulation is 8% or less.
3. The method according to claim 1, wherein a sugar alcohol and a water-swelling additive are used as the excipients.

4. The method according to claim 1, wherein the sugar alcohol is mannitol.

5. The method according to claim 1, wherein the water-swelling additive is pregelatinized starch.

6. The method according to claim 1, wherein the sugar alcohol is mannitol, and the water-swelling additive is pregelatinized starch.

7. The method according to claim 1, wherein the disintegrant is crospovidone.

8. The method according to claim 1, wherein the binder is hydroxypropyl cellulose.

9. The method according to claim 1, wherein the component (A) is $N^1$-(5-chloropyridin-2-yl)-$N^2$-(1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl) ethanediamide p-toluenesulfonate monohydrate represented by the following formula (Ia):

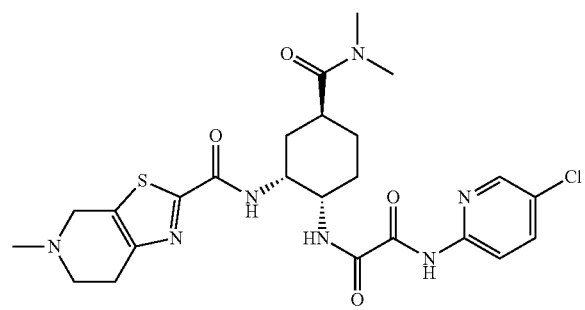

(Ia)

-continued

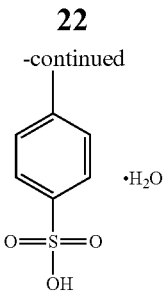

·$H_2O$

10. The method according to claim 1, further comprising the step of drying the obtained granules.

11. The method according to claim 1, further comprising a coating step after the granulation step.

12. The method according to claim 11, wherein the coating agent is one or more coating agents selected from the group consisting of a cellulose derivative and a polyvinyl compound.

13. The method according to claim 11, wherein the coating agent is one or more coating agents selected from the group consisting of hypromellose, ethyl cellulose, and polyvinyl alcohol.

14. The method according to claim 1, wherein when the composition is subjected to a dissolution test by the paddle method at a rotation speed of 50 rpm, the composition exhibits an mean dissolution rate of the compound represented by formula (I), in a dissolution medium having a pH of 6.8, of 70% or higher in 30 minutes after the start of the dissolution test and 80% or higher in 60 minutes after the start.

\* \* \* \* \*